United States Patent [19]
Johnston

[11] Patent Number: 6,146,405
[45] Date of Patent: Nov. 14, 2000

[54] OPHTHALMIC APPLANATOR

[76] Inventor: Robert M. Johnston, 1099 River Rd., Bluemont, Va. 20135

[21] Appl. No.: 09/247,945

[22] Filed: Feb. 11, 1999

[51] Int. Cl.[7] ....................................................... A61B 5/00
[52] U.S. Cl. ....................................................... 606/204.25
[58] Field of Search ..................................... 600/405, 406; 606/4, 5, 13, 17, 107, 166, 191, 204.25; 351/159, 177, 178

[56] References Cited

U.S. PATENT DOCUMENTS

| | | |
|---|---|---|
| 2,117,312 | 5/1938 | Gauly . |
| 5,021,057 | 6/1991 | Byrne, Jr. . |
| 5,549,632 | 8/1996 | Lai . |
| 5,984,916 | 11/1999 | Lai .......................................... 606/11 |

*Primary Examiner*—Max Hindenburg
*Attorney, Agent, or Firm*—Larson & Taylor, PLC

[57] ABSTRACT

An ophthalmic applanator for treatment of corneal lamellar flaps/caps includes a disc having a concave bottom surface with a curvature flatter than the curvature of the external surface of the cornea of the eye and steeper than the curvature of the surface of the sclera of an eye and a concave or convex top surface. The radius of curvature of the bottom surface produces a radiating pressure of higher magnitude centrally than peripherally, but is also curved sufficiently to minimize the risk of excessive indentation of the cornea. The convex or concave upper surface reduces reflection from the operating microscope.

14 Claims, 3 Drawing Sheets

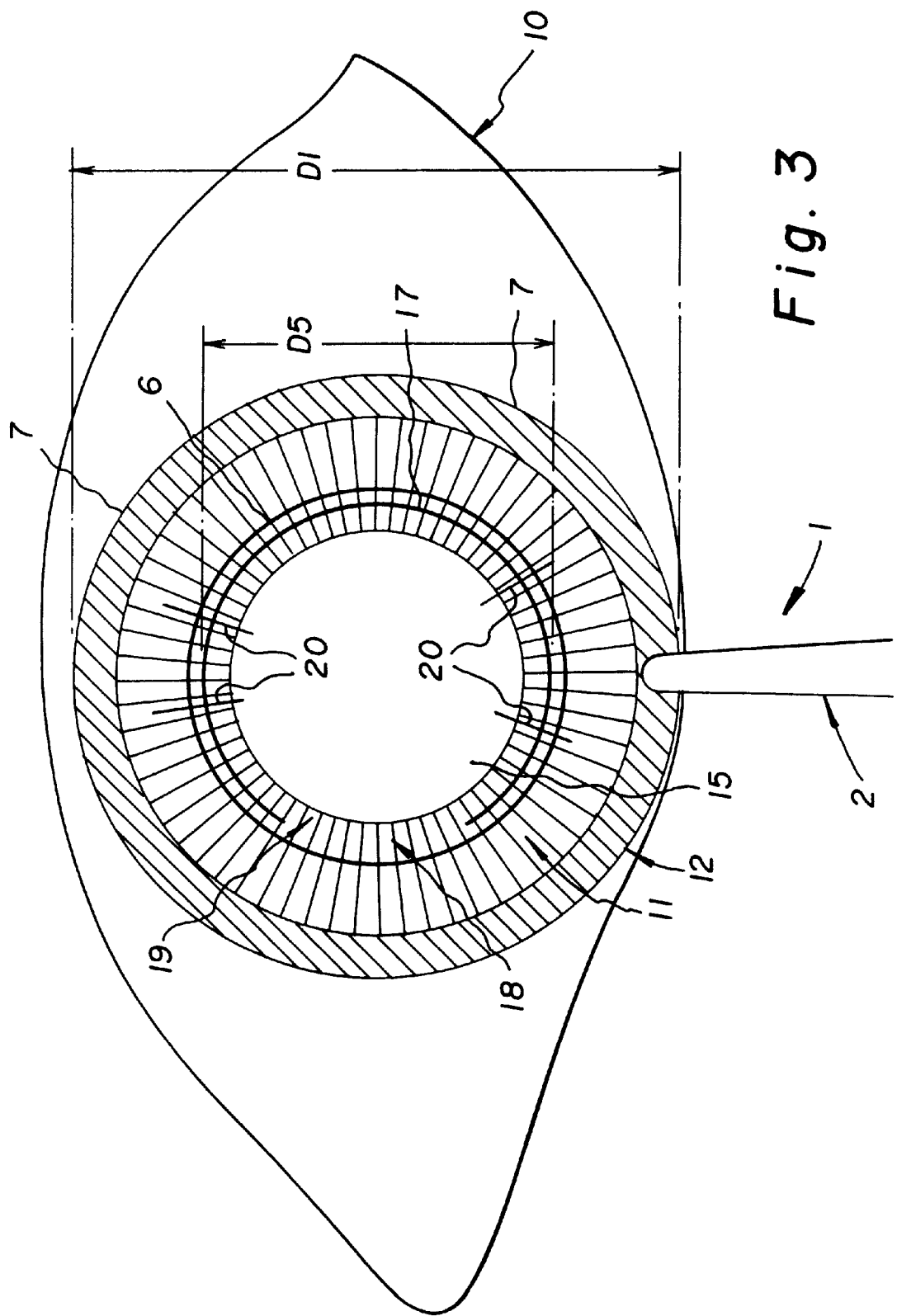

OPHTHALMIC APPLANATOR

FIELD OF THE INVENTION

The present invention relates to an ophthalmic applanator and a method of use thereof and, more particularly, to a device which effects consistent, post-operative optical clarity and performance in the positioning of a corneal lamellar flap or cap.

BACKGROUND OF THE INVENTION

Corneal lamellar flap or cap complications are a problem which occur in corneal lamellar surgical procedures. Flap complications are particularly problematic in laser assisted in situ keratomileusis ("LASIK") procedures. During a LASIK procedure, a superficial corneal flap is elevated in order to maintain the integrity of the corneal surface tissues and allow access to the deeper corneal stroma where laser energy application selectively removes tissue in a pattern and quantity sufficient to correct a refractive error, such as myopia, hyperopia or astigmatism. After the laser tissue ablation, the flap is laid back over the stromal bed. As a result of the tissue removal, there is a disparity in shape between the flap and the bed necessitating positioning of the flap.

One prior art method used at the conclusion of a LASIK procedure for positioning the corneal flap is known as "painting" which is performed using a small, moist, cellulose sponge, known as a Merocel sponge. This procedure reduces the fluid under the corneal flap and positions the flap on the stromal bed. Alternative devices which are often used for positioning the corneal flap include a small wire roller, a glass rod, a large curette, a glass marble or any other convex surface which is slightly larger than the cornea. However, regardless of the device which is utilized, current techniques do not yield consistent results and problems, such as improper seating and healing of the flap and resultant striae, often arise. A second surgery to re-float or reposition the corneal flap is then required.

Accordingly, there is a need for a device which may be used any time a corneal lamellar flap or cap requires positioning to effect consistent post-operative optical clarity and performance.

SUMMARY OF THE INVENTION

Thus, it is a purpose of the present invention to overcome the disadvantages of the prior art and thereby provide a device which may be used by surgeons for prevention of corneal flap or cap complications at the conclusion of a surgical procedure as well as for treatment of complications which may occur at some time after a surgical procedure involving the cornea.

In accordance with a preferred embodiment of the invention, the device includes a disc having a concave bottom surface and either a concave or a convex top surface. The concave bottom surface has a curvature which is flatter than the curvature of the surface of the external surface of the cornea of the eye and steeper than the curvature of the surface of the sclera of the eye. A handle is attached to the disc via a retaining ring which holds the disc.

Preferably, the radius of curvature of the bottom surface of the disc is at least 15 millimeters (mm), more preferably 20 mm, and the top surface is convex with a radius of curvature of at least 15 mm, preferably 30 mm. The disc should comprise a transparent material, both the top and bottom surfaces being polished. The disc may further include a marking on one of the top and bottom surfaces, to improve the surgeon's ability to assess the area of applanation. Preferably, the marking is a scribed or painted circle having the same center as that of the disc.

In a method of positioning a corneal flap or cap in accordance with the invention, pressure is applied to a cornea of an eye using an applanator comprising a disc having a concave bottom surface and a concave or a convex top surface, the concave bottom surface having a curvature flatter than the curvature of the external surface of the cornea of an eye and steeper than the curvature of the surface of the sclera of an eye.

It is, therefore, an object of the invention to provide a device for deforming the cornea of an eye based on a selected radius of curvature to effect a more physiologic approximation of the semi- or fully detached corneal tissue to the underlying tissue.

It is another object of the invention to provide a method of using an ophthalmic applanator to seat a corneal flap or cap using a minimum of time and surgical skill.

These and other objects of the present invention will become apparent from the detailed description to follow.

BRIEF DESCRIPTION OF THE DRAWINGS

There follows a detailed description of the preferred embodiments of the invention which are to be take together with the accompanying drawings wherein:

FIG. 3 is a top view of the ophthalmic applanator during a corneal flap positioning procedure.

DETAILED DESCRIPTION OF THE PREFERRED EMBODIMENTS

The applanator of the invention may be used for treatment of corneal flaps or caps. However, only the term "flap" is used throughout the description for convenience.

Referring now to the figures, like elements are represented by like numerals throughout the several views.

Figure 1:
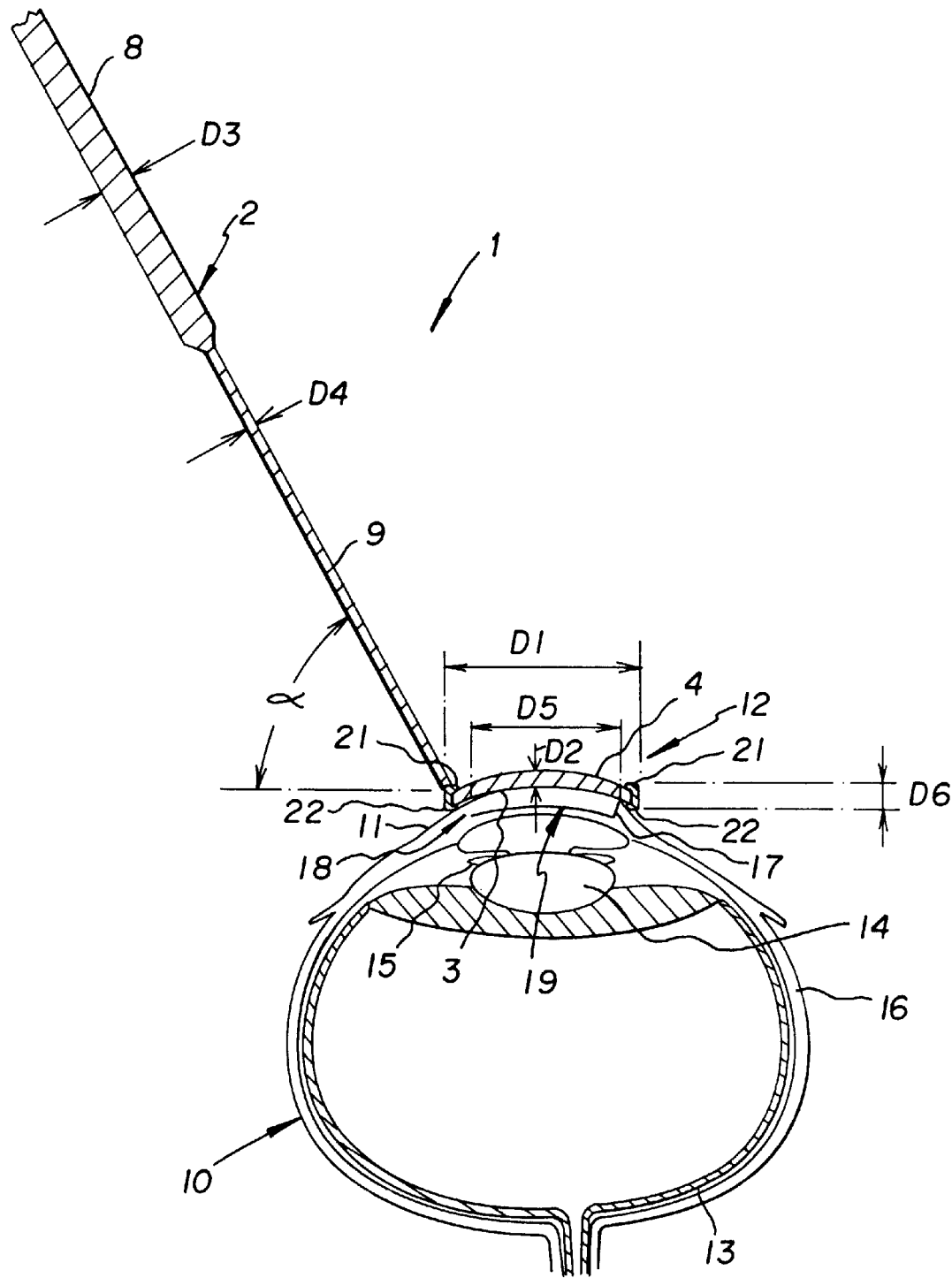
FIG. 1 is a side elevational view of the ophthalmic applanator of the invention positioned over the cornea of an eye, the applanator being shown in cross-section.

As shown in FIG. 1, the ophthalmic applanator 1 of the invention includes a disc 12 attached to a handle 2. During a surgical procedure, the bottom surface 3 of the disc 12 is placed against the eye 10 and light from the operating microscope (not shown) is directed through the top surface 4 of the disc 12. The disc 12 is seated in a retaining ring 7. The diameter D1 of the retaining ring should not exceed 15 mm in order to fit comfortably within the palpebral fissure of the eye 10. However, the diameter of the disc 12 should be at least 11.5 mm to cover the entire corneal surface 11. The disc 12 is most preferably about 13 mm in diameter. The 13 mm diameter is suitable for treatment of all corneal flap sizes, since the typical diameter D5 of a myopic flap is 8.5–9 mm and the typical hyperopic flap is 10–10.5 mm in diameter, with the corneal diameter of the adult eye ranging from approximately 11–13 mm. The applanator of the invention is equally suitable for use in surgical procedures on a child's cornea, which has a diameter of about 10–12 mm.

The top surface 4 of the disc 1 is preferably concave or convex, as opposed to plano, in order to minimize back reflection into the surgeon's eye which interferes with his ability to visualize the deeper surfaces being treated, as well as to alter the focusing power of the applanator 1 in a manner to prevent concentration of light on the retina 13. In the most preferred embodiment, the top surface 4 is convex and has a radius of curvature of at least 30 mm.

The bottom surface 3 is concave to permit better centration of the cornea 11 during applanation and to minimize the posterior deflection and distortion of the cornea 11, thereby reducing the risk of damage to the endothelium and intraocular structures such as the lens 14 and iris 15. The bottom surface 3 has a single curvature that is flatter than the curvature of the external surface of the cornea 11 of an eye and steeper than the curvature of the surface of the sclera 16 of an eye. Preferably, the radius of curvature is between 15 mm and 40 mm, even more preferably between 18 mm and 25 mm, with 20 mm being optimal. The radius of curvature of the bottom surface 3 provides a radiating pattern of pressure over a corneal flap such that the bottom surface 3 need not be changed according to the type of correction undertaken. In other words, the applanator 1 may be used for myopic treatment in which ablation takes place in the central 6 mm of the cornea 11, as well as for hyperopic ablation in which the annular area of ablation extends from approximately 2.5–4.5 mm from the center of the cornea 11. Thus, the applanator 1 of the invention is suitable not only for LASIK procedures, but also for techniques such as automated lamellar keratectomy, lamellar corneal transplants, or any other procedure in which it is desirable to provide a uniform surface of contact between a lamellar piece of corneal tissue and the underlying bed.

Disc 12 is preferably constructed of a transparent material. Most preferably, the disc 12 is constructed of glass, which is durable when subjected to autoclaving and cleansing. However, disc 12 may also be constructed of a plastic material, typically a non-thermal transparent tooled or molded plastic, such as polymethyl methacrylate ("PMMA") or Ultima. Preferably, the disc 12 is also polished on the top 4 and bottom 3, such that it is optically clear allowing the applanated surface to be viewed through the operating microscope. The thickness D2 of the disc 12 may range from 1 to 3 mm. Preferably the depth D6 of retaining ring 7, as well as the thickness of the edges of the disc 12, do not exceed about 1.5 mm.

Figure 2:
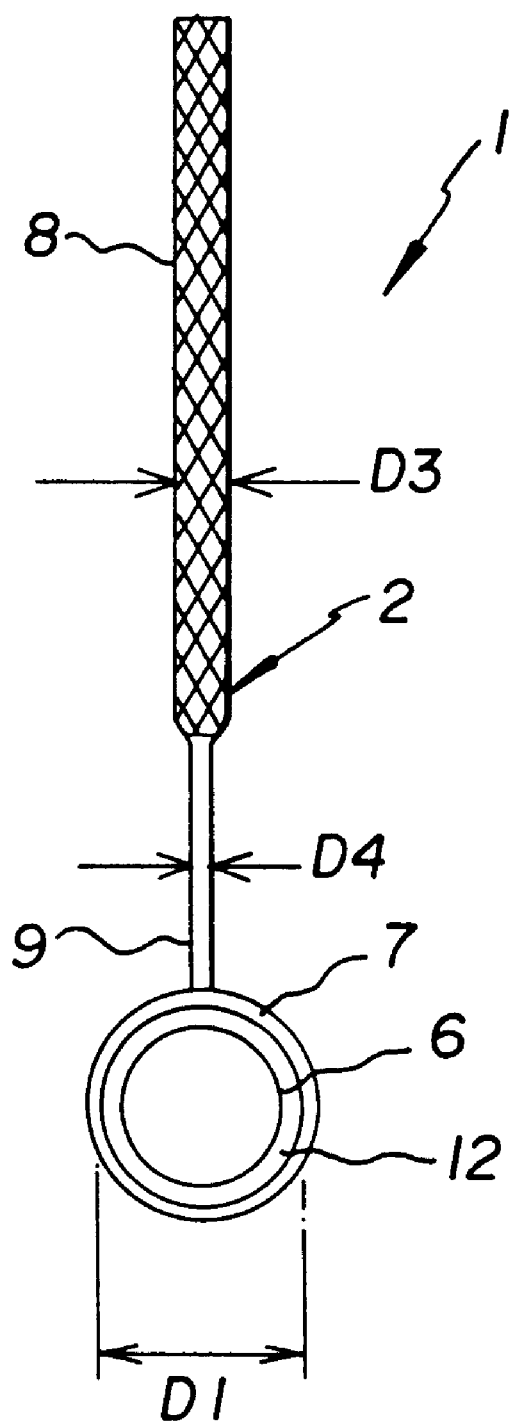
FIG. 2 is a top view of the ophthalmic applanator of the invention.

In order to better assess the area of applanation, a marking may be located on either the top surface 4 or bottom surface 3 of the disc 12. In a preferred embodiment, shown in FIG. 2, the marking is a scribed or painted circle 6 having the same center as the disc 12, and preferably has a diameter of about 5 mm (to approximate the pupil size) to 10 mm (to approximate the flap diameter). A 9 mm diameter is most preferable as it is slightly greater than the diameter of the average myopic flap and slightly less than the diameter of the average hyperopic flap.

Retaining ring 7 facilitates attachment of the disc 12 to the handle 2. The retaining ring 7 may be constructed of any material, but is preferably made of surgical stainless steel, e.g., 316 ss, which is strong and durable, but not as costly as other materials such as titanium. The surface of the retaining ring 7 is burnished in order to eliminate reflection or glare. Handle 2 should be attached to the retaining ring 7 so as to minimize intrusion into or obscuration of the optical portion of the disc 12 and to reduce interference with the patient's nose, yet allow sufficient downward depression onto the corneal surface 11. It has been found that the optimal angle α of attachment of the handle 2 to the disc 12 is between 50° and 70°, most preferably 60°, from a horizontal plane parallel to the top 21 or bottom 22 surfaces of the retaining ring 7. The handle 2 may be constructed of any material, such as surgical stainless steel or titanium. In a preferred embodiment, the upper end 8 of handle 2 is cylindrical and has a diameter D3 of about 2.5 mm with a knurled surface to provide a surface which is easily gripped by the surgeon. In order to reduce the weight and bulk of the handle 2, the thickness of the handle 2 is reduced at the lower end 9 to a diameter D4 of about 1.5 mm and has a smooth surface. In a preferred embodiment, the total length of the handle 2 is about 80–125 mm, typically 105 mm. The upper end 8 is generally 75–100 mm, preferably 85 mm, in length and the lower end 9 is about 5–35 mm, preferably 20 mm, in length.

Referring to FIG. 3, in a method of using the ophthalmic applanator 1 of the invention, pressure is applied to the cornea 11 of an eye 10 with the concave bottom surface 3 of the disc 12. Through a slight rotation of the surgeon's wrist, the applanating force is distributed over the surface of the corneal flap 19 until the entire flap 19 has been applanated. No further manipulation of the corneal flap 19 is required and the flap 19 will seat itself over a one to two minute period prior to removal of the lid speculum. Since the disc 12 is constructed of a transparent material, it is possible to view the area of applanation through the disc 12. The scribed circle 6 further helps to identify the area of applanation and flap alignment marks 20.

In re-floating and repositioning procedures, the eye 10 is approached under the operating microscope, the lid speculum is inserted, and the edge 17 of the flap 19 is elevated using a semi-sharp instrument to penetrate the existing scar at the flap edge 17. Another instrument is then used to extend this initial elevating wound around the entire edge of the flap 19. The flap 19 is elevated with forceps or by undermining with a cannula and reflected back about the hinge 18. The interface may then be treated with additional laser applications if an enhancement procedure is required, irrigated to remove interface debris, or curetted to debrid in-growth of epithelium. The flap 19 is then repositioned and the applanator 1 is applied in the same manner as described above. The interface may be irrigated before application of the applanator 1. If the purpose of re-floating and repositioning the flap 19 is the existence of striae, then pressure is applied for a full two minute interval with the applanator 1. That is, pressure is transmitted by way of the applanator 1 to the corneal flap in order to apply lines of force sufficient to even out the striae.

Using the applanator 1 of the invention, there is no need for intervention with Merocel sponges, which may threaten the stability of the flap repositioning. The alignment of the previously placed corneal flap alignment marks 20 may be observed and, if there is any disparity, the interface may be irrigated again and the applanator 1 reapplied.

Although the invention has been described in considerable detail with respect to preferred embodiments thereof, variations and modifications will be apparent to those skilled in the art without departing from the spirit and scope of the invention as set forth in the claims.

What is claimed is:

1. An ophthalmic applanator comprising:
    a disc having a concave bottom surface and a top surface selected from the group consisting of a convex surface and a concave surface, said concave bottom surface having a curvature flatter than a curvature of the external surface of the cornea of an eye and steeper than a curvature of the surface of the sclera of an eye; and
    a handle attached to said disc.

2. The ophthalmic applanator according to claim 1 wherein said disc is seated in a retaining ring, said handle being attached to said retaining ring.

3. The ophthalmic applanator according to claim 2 wherein said handle is attached to said retaining ring at an angle of 50–70° from a horizontal plane parallel to a bottom or a top surface of said ring.

4. The ophthalmic applanator according to claim 1 wherein the radius of curvature of said bottom surface is 15–40 mm.

5. The ophthalmic applanator according to claim 4 wherein the radius of curvature of said bottom surface is at least 20 mm.

6. The ophthalmic applanator according to claim 1 wherein said top surface is convex and has a radius of curvature of at least 30 mm.

7. The ophthalmic applanator according to claim 1 wherein said top surface and said bottom surface are polished.

8. The ophthalmic applanator according to claim 1 wherein said disc has a diameter of 11.5–15 mm.

9. The ophthalmic applanator according to claim 1 wherein said disc comprises a transparent material.

10. The ophthalmic applanator according to claim 9 wherein said material is selected from the group consisting of glass and non-thermal transparent tooled or molded plastic.

11. The ophthalmic applanator according to claim 9 wherein said disc includes a circle marked thereon having a same center as said disc on one of the top and the bottom surfaces.

12. A method of positioning a corneal flap or cap comprising:

applying pressure to a corneal flap or cap with an applanator comprising a disc having a concave bottom surface and a top surface selected from the group consisting of a convex surface and a concave surface, said concave bottom surface having a curvature flatter than a curvature of the external surface of a cornea of an eye and steeper than a curvature of the surface of a sclera of an eye, and a handle attached to said disc.

13. The method according to claim 12 wherein pressure is applied for one to two seconds to complete seating of the corneal flap or cap.

14. The method according to claim 12 wherein said pressure is applied for two minutes to eliminate striae.

* * * * *